United States Patent [19] [11] 4,062,866

Garner et al. [45] Dec. 13, 1977

[54] 3-INDOLYL-3-PHENYL-PHTHALIDES

[75] Inventors: Robert Garner, Bury, England; Jean Claude Petitpierre, Kaiseraugst, Switzerland

[73] Assignee: Ciba-Geigy Corporation, Ardsley, N.Y.

[21] Appl. No.: 686,863

[22] Filed: May 17, 1976

Related U.S. Application Data

[63] Continuation of Ser. No. 471,395, May 20, 1974, abandoned.

[30] Foreign Application Priority Data

May 21, 1973 United Kingdom ............... 24077/73

[51] Int. Cl.[2] ............................................ C07D 209/20

[52] U.S. Cl. .......................... 260/326.14 R; 106/14.5; 106/21; 106/22

[58] Field of Search ............................... 260/326.14 R

[56] References Cited

U.S. PATENT DOCUMENTS

| | | | |
|---|---|---|---|
| 3,540,911 | 11/1970 | Lin | 260/326.14 R |
| 3,736,337 | 5/1973 | Farber | 260/326.14 R X |
| 3,829,322 | 8/1974 | Ozutsumi et al. | 260/326.14 R X |

*Primary Examiner*—Ethel G. Love
*Attorney, Agent, or Firm*—Prabodh I. Almaula; Edward McC. Roberts

[57] ABSTRACT

Phthalides of the formula

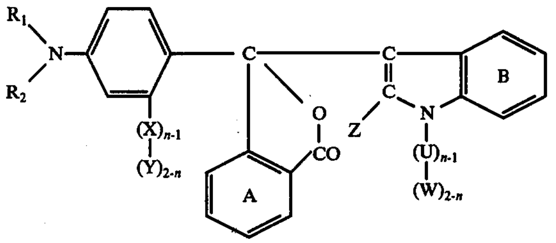

wherein $R_1$ and $R_2$, independently of the other, represent hydrogen, alkyl with 1 to 12 carbon atoms, alkoxyalkyl with 2 to 8 carbon atoms, cycloalkyl with 5 or 6 carbon atoms, benzyl or phenyl, X represents alkyl with 1 to 12 carbon atoms, alkoxy with 1 to 12 carbon atoms or acyloxy with 2 to 12 carbon atoms, Y represents alkyl with 2 to 12 carbon atoms, alkoxy with 3 to 12 carbon atoms or acyloxy with 2 to 12 carbon atoms, Z represents hydrogen, alkyl having 1 to 12 carbon atoms or phenyl, U represents alkyl having 3 to 12 carbon atoms, benzyl or cyanoethyl, or may also represent W when $R_1$ and $R_2$ both are benzyl, W represents hydrogen, methyl or ethyl and *n* is 1 or 2, the benzene rings A and B may be substituted by an amino group optionally substituted by alkyl with 1 to 6 carbon atoms and the benzene ring B may also be substituted by nitro or halogen.

The phthalides are particularly useful as color formers which give intense blue colors when they are contacted with an electron-accepting co-reactant such as silton clay or a phenolic resin.

8 Claims, No Drawings

3-INDOLYL-3-PHENYL-PHTHALIDES

This is a continuation of application Ser. No. 471,395, filed on May 20, 1974, now abandoned.

The present invention provides novel chromogenic compounds which are normally colourless or only weakly coloured but which give intense blue colours when contacted with an electron-accepting co-reactant. The invention specifically relates to novel 3-indolyl-3-phenyl-phthalides, the manufacture of such compounds, and their use as color formers in pressure-sensitive copying material.

The most widely used blue color former is Crystal Violet Lactone (CVL) which is usually used in admixture with benzoyl leuco methylene blue to compensate for the poor stability of the former.

It is the object of this invention to provide a blue color former having improved properties to CVL.

This is provided by a series of compounds having the formula (1)

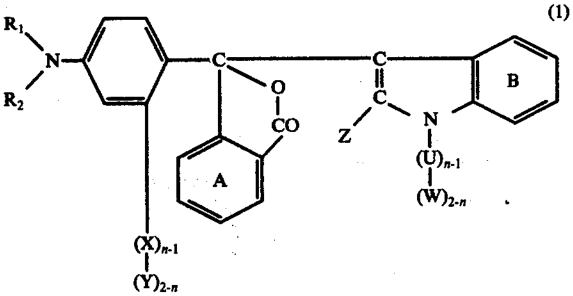

wherein $R_1$ and $R_2$, independently of the other, represent hydrogen, alkyl with 1 to 12 carbon atoms, alkoxyalkyl with 2 to 8 carbon atoms, cycloalkyl with 5 or 6 carbon atoms, benzyl or phenyl, X represents alkyl with 1 to 12 carbon atoms, alkoxy with 1 to 12 carbon atoms or acyloxy with 2 to 12 carbon atoms, Y represents alkyl with 2 to 12 carbon atoms, alkoxy with 3 to 12 carbon atoms or acyloxy with 2 to 12 carbon atoms, Z represents hydrogen, alkyl having 1 to 12 carbon atoms or phenyl, U represents alkyl having 3 to 12 carbon atoms, benzyl or cyanoethyl, or U may also be W, when $R_1$ and $R_2$ both are benzyl, W represents hydrogen, methyl or ethyl and *n* is 1 or 2, the benzene rings A and B may be substituted by an amino group optionally substituted by alkyl with 1 to 6 carbon atoms and the benzene ring B may also be substituted by nitro or halogen.

Amongst the 3-indolyl-3-phenyl-phthalides which lie within the compass of formula (1) those compounds of formula (1*a*)

(1a)

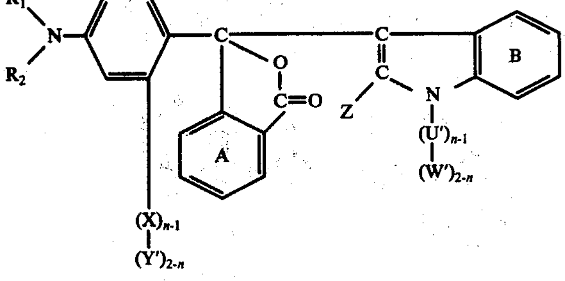

wherein

U' represents alkyl having 5 to 12 carbon atoms, especially 7 to 12 carbon atoms, benzyl or cyanoethyl or also W when $R_1$ and $R_2$ both are benzyl, Y' represents alkyl having 5 to 12 carbon atoms, especially 7 to 12 carbon atoms, alkoxy having 5 to 12 carbon atoms, especially 7 to 12 carbon atoms, or acyloxy with 2 to 12 carbon atoms, especially 2 to 4 carbon atoms, W' represents hydrogen or alkyl having 1 to 6, especially 1 to 4 carbon atoms, and $R_1$, $R_2$, X, Z, A, B and *n* have the meanings given above, should be particularly singled out.

Practically important groups of the compounds of the formulae (I) and (I*a*) may be defined by the two following formulae (2)

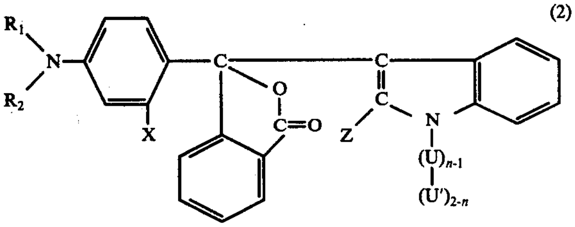

(3)

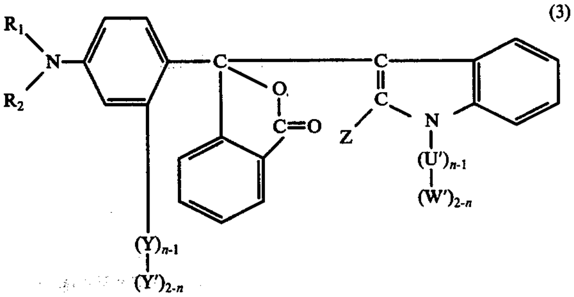

wherein *n*, $R_1$, $R_2$, X, Y, Y', Z, U, U', W and W' have the meanings given above.

When the radicals $R_1$, $R_2$, $R_3$ and $R_4$ represents alkyl, they may be straight or branched chain alkyl groups. Examples of said alkyl groups are methyl, ethyl, n-propyl, isopropyl, n-butyl or sec-butyl, octyl or dodecyl. Alkoxyalkyl in $R_1$, $R_2$, $R_3$ and $R_4$ may have 1 to 4 carbon atoms in each alkyl part and stands preferably for β-methoxyethyl or α-ethoxyethyl. Cycloalkyl in the meanings of these R-radicals may be cyclopentyl or preferably cyclohexyl. As alkyl and alkoxy, X is preferably methyl, methoxy and ethoxy while Y represents advantageously a higher alkyl or alkoxy group. Among the acyloxy groups the alkanoyloxy groups containing 2 to 4 carbon atoms, such as acetyloxy or propionyloxy, are especially noteworthy.

Alkyl in Z may be methyl, ethyl, n-butyl, octyl or dodecyl, in U it preferably has from 5 to 12, most preferably 7 to 12 carbon atoms such as octyl or dodecyl. The benzene rings A and B may contain as substituted amino group a dimethylamino, diethylamino or n-hexylamino group. A halogen substituent may be fluorine, bromine or especially chlorine.

Particularly valuable phthalide compounds of the formula (1) are those 3-indolyl-3-phenyl phthalides which are listed under (A) and (B) respectively.

A. Compounds of the formula (4)

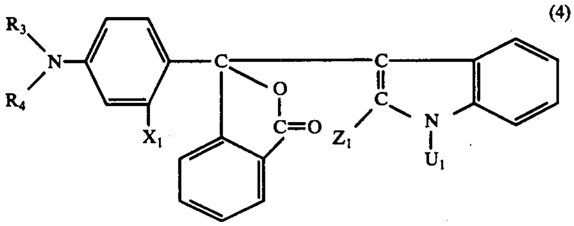

wherein $R_3$ and $R_4$ independently of the other represent hydrogen, alkyl with 1 to 4 carbon atoms, cyclohexyl, benzyl or phenyl, $X_1$ represents methyl, alkoxy with 1 to 12 carbon atoms or alkanoyloxy with 2 to 4 carbon atoms, $Z_1$ represents hydrogen, alkyl having 1 to 4 carbon atoms or phenyl and $U_1$ represents alkyl having 3 to 8 carbon atoms, especially 5 to 8 carbon atoms, benzyl or also methyl or ethyl when $R_3$ and $R_4$ both are benzyl.

B. Compounds of the formula (5)

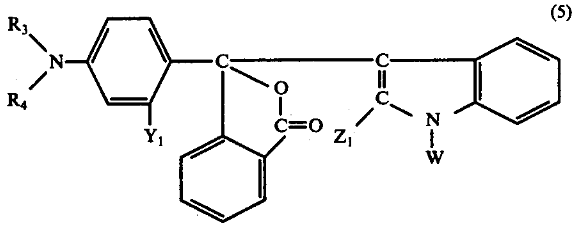

wherein $R_3$, $R_4$, $Z_1$ and W have the given meanings and $Y_1$ represents alkoxy with 3 to 12 carbon atoms preferably with 5 to 12 carbon atoms, or alkanoyloxy with 2 to 4 carbon atoms.

Within the above formulae two important subgroups should be mentioned especially, in one of which the N-substituent in the indolyl grouping has at least 3 carbon atoms, especially at least 7 carbon atoms (Type C) while the other group contains as N-substituent of the indole ring methyl or ethyl (Type D).

C. Compounds of the formula (6)

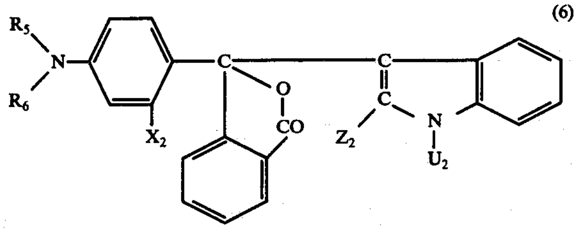

wherein $R_5$ and $R_6$ independently of the other represent alkyl with 1 to 4 carbon atoms or benzyl, $X_2$ represents methyl, alkoxy with 1 to 4 carbon atoms, or alkanoyloxy with 2 to 4 carbon atoms, $Z_2$ represents methyl or phenyl and $U_2$ represents alkyl having 3 to 8 carbon atoms especially having 7 or 8 carbon atoms.

D. Compounds of the formula (7)

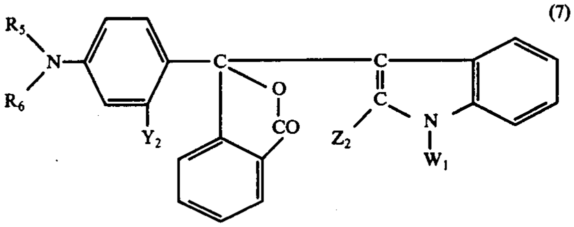

wherein $R_5$, $R_6$ and $Z_2$ have the meanings given above and $Y_2$ represents alkanoyloxy with 2 to 4 carbon atoms, and $W_1$ represents methyl or ethyl.

The new phthalide compounds of the formulae (1) to (7) are accessible by known methods.

In general, the phthalide compounds according to the invention are manufactured by reacting a benzophenone compound of the formula (8)

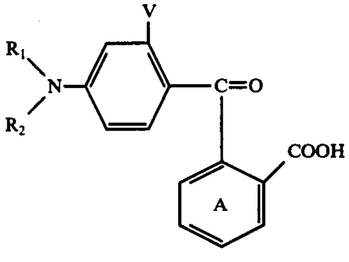

with an indole compound of the formula (9)

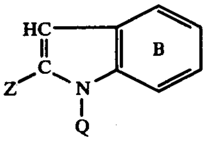

wherein A, B, $R_1$, $R_2$ and Z have the given meanings, V has the meaning given for X and Y or also hydroxy, and Q has the meaning given for U and W, and alkylating or acylating the reaction product when V is hydroxy. The reaction is carried out by allowing the reactants to react together in the presence of an acidic condensing agent. Examples of suitable condensing agents are acetic anhydride, sulphuric acid and zinc chloride or phosphorus oxychloride.

Alternatively, the phthalide compounds according to the invention may be obtained by reacting a carboxybenzoyl indole compound of the formula (10)

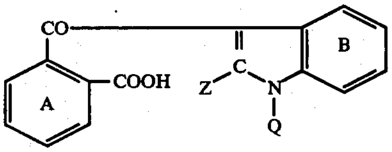

with an aniline compound of the formula

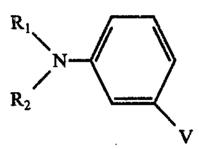

(11)

wherein A, B, $R_1$, $R_2$, V, Q and Z have the given meanings, and alkylating or acylating the reaction product when V is hydroxy.

The starting compounds of the formulae (8) and (10) are generally prepared by reacting phthalic anhydride with an aniline compound of the formula (11) and with an indole compound of formula (9) respectively, desirably in an organic solvent optionally in the presence of a metal halide of the Lewis acids. Suitable organic solvents are for example benzene, toluene, xylene, a chlorobenzene or carbon disulphide. Among the metal halides of Lewis acids aluminium chloride is prefereed. The compounds of formula (8) wherein V is alkoxy or acyloxy are preferably obtained by alkylating or acylating according to conventional methods the intermediate products prepared by reacting phthalic anhydride with an aniline compound of formula (11) wherein V is hydroxy. The acylation and the alkylation of the intermediate compounds wherein V is hydroxy, is desirably carried out with acylating and alkylating agents, respectively, having at most 12 carbon atoms. Acylating agents which can be used here are, e.g., reactive functional derivatives of aliphatic carboxylic acids, particularly fatty acids halides and anhydrides, such as acetyl bromide, acetyl chloride or acetic anhydride. Alkylating agents may be alkyl halides such as methyl or ethyl iodide or chloride. The acylation and the alkylation are generally carried out by known methods e.g. in the presence of acid binding agents such as alkali metal carbonates or tertiary nitrogen bases such as pyridine and optionally in the presence of inert organic solvents such as chlorobenzene or nitrobenzene.

The new phthalides according to the invention are more or less colorless compounds which are particularly useful as so-called color formers. The term "color former" is used to describe a compound which is normally colorless or very faintly colored but which produces a strong color when it is brought into contact with a co-reactive substrate which is an electron acceptor. Typical co-reactants are, for example, attapulgus clay, silton clay, silica, bentonite, halloysite, aluminum oxide, aluminum phosphate, kaolin or any acidic clay, or an acid reacting polymeric material such as a phenolic polymer, an alkylphenolacetylene resin, a maleic acid-rosin resin or a partially or wholly hydrolyzed polymer of maleic anhydride with styrene, ethylene, vinyl methyl ether or carboxy polymethylenes.

The preferred co-reactants are attapulgus clay, silton clay, silica or a phenol-formaldehyde resin. These electron acceptors, preferably, are coated on the front side of the receiving sheet electron accepting substance.

With the new color formers according to the invention a large variety of blue or blue-green colors may be produced.

In comparison with the well-known CVL the compounds are of similar intensity. Phthalide compounds of formula (1) in which X or Y denotes an acyloxy group show a little greener shade while the phthalide compounds where X or Y are an alkoxy group are in general a little redder in shade.

The present color formers show an improved lightfastness, both on clay and phenolic substrates. With the present new phthalides a further range of color formers is provided with solubilities such as to allow greater flexibility in choice of solvents used for encapsulations and other modes of applications.

Pressure-sensitive recording material may be of several kinds well known in the art and for example may consist of sheets of paper coated with microcapsules containing a solution of the color formers. When these capsules are ruptured by pressure from writing, printing, or typing, the color former is brought into contact with an acidic substance which is coated on the same or on an adjacent sheet thus producing an image which is a fine copy of the original.

The above example is only one of a variety of modes of application, the microcapsules may instead be contained in the base web or indeed as an alternative to encapsulation the solution of color former may be protected from premature reaction by any other means such as entrapment in a foam-like layer or as an emulsion in a hardened film.

As already mentioned, these color formers above all are suitable for the use in so-called pressure-sensitive copying or recording material. Such a material, e.g., includes at least one pair of sheets, which comprises at least a color former of formula (1) or of the surbordinate formulae dissolved in an organic solvent, preferably contained in pressure rupturable microcapsules and an electron accepting substance. The color former, upon coming into contact with the electron accepting substance produces a colored mark at the points where the pressure is applied.

These color formers which are comprised in the pressure-sensitive copying material are prevented from becoming active by being separated from the electron accepting substance. As a rule this is done by incorporating these color formers into a foam-, sponge- or honey-comb-like structure. Preferably however these color formers are microencapsulated.

When these colorless color formers of formula (1) are dissolved in an organic solvent, they may be subjected to a microencapsulation process and subsequently used for making pressure sensitive papers. When the capsules are ruptured by pressure from, e.g., a pencil, and the color former solution is thus transferred onto an adjacent sheet coated with a substrate capable of acting as an electron acceptor, a colored image is produced. This color results from the dyestuff thus produced, which absorbs in the visible region of the electromagnetic spectrum.

The general art of making microcapsules of some character has long been known. Well known methods, e.g., are disclosed in U.S. Pat. Nos. 2,183,053, 2,800,457, 2,800,458, 3,265,630, 2,964,331, 3,418,656, 3,418,250, 3,016,308, 3,424,827, 3,427,250, 3,405,071, 3,171,878 and 2,797,201. Further methods are disclosed in British patent specifications Nos. 989,264 and above all 1,156,725. Any of these and other methods are suitable for encapsulating the present color formers.

Preferably the present color formers are encapsulated dissolved in organic solvents. Suitable solvents are preferably non-volatile, e.g., polyhalogenated diphenyl such as trichlorodiphenyl and its mixture with liquid paraffin, tricresyl, phosphate, di-n-butyl phthalate, dioctyl phthalate, trichlorobenzene, nitrobenzene, trichloroethyl-phosphate, petroleum ether, hydrocarbon oils, such as paraffin, condensed derivatives of diphenyl or triphenyl, chlorinated or hydrogenated condensed aromatic hydrocarbons. The capsule walls preferably have been obtained by coacervation forces evenly around the droplets of the color former solution, the encapsulating material consisting of gelatine, as, e.g., described in U.S. Pat. No. 2,800,457.

Alternatively, the capsules preferably may be made of aminoplast or modified aminoplasts by polycondensation as described in British patent specification Nos. 989,264 or 1,156,725.

A preferred arrangement is wherein the encapsulated color former is coated on the back side of a transfer sheet and the electron accepting substance is coated on the front side of a receiving sheet.

In another preferred material the new 3-indolyl-3-phenyl phthalides are co-encapsulated with one or more other known color formers such as crystal violet lactone, 3,3-bis(1'-n-octyl-2'-methylindol-3'-yl)-phthalide or benzoyl leuco methylene blue.

The microcapsules containing the color formers of formula (1) or of the subordinate formulae are used for making pressure-sensitive copying material of the various types known in the art, such as so-called "Chemical Transfer" and "Chemical Self-contained" papers. The various systems mainly are distinguished by the arrangement of the capsules, the color reactants and the support material.

The microcapsules may be in a undercoating of the upper sheet and the color reactants, that is the electron acceptor and coupler, may be in the overcoating of the lower sheets. However, the components may also be used in the paper pulp. Such systems are called "Chemical Transfer"-system.

Another arrangement we have in the self-contained papers. There the microcapsules containing the color former and the color reactants are in or on the same sheet as one or more individual coatings or in the paper pulp.

Such pressure-sensitive copying materials are described, e.g., in U.S. Pat. Nos. 3,516,846, 2,730,457, 2,932,582, 3,427,180, 3,418,250 and 3,418,656. Further systems are disclosed in British patent specification Nos. 1,042,597, 1,042,598, 1,042,596, 1,042,599, 1,053,935 and 1,517,650. Microcapsules containing the color formers of formula (1) are suitable for any of these and other systems.

The capsules are preferably fixed to the carrier by means of a suitable adhesive. Since paper is the preferred carrier material, these adhesives are predominantly paper coating agents, such as, e.g., gum arabic, polyvinyl alcohol, hydroxymethylcellulose, casein, methylcellulose or dextrin.

In the present application, the definition "paper" not only includes normal papers from cellulose fibres, but also papers in which the cellulose fibres are replaced (partially or completely) by synthetic fibres of polymers.

The following non-limitative examples illustrate the present invention. Percentages are expressed by weight unless otherwise stated.

EXAMPLE 1

3-(4'-Diethylamino-2'-ethoxyphenyl)-3-(1"-n-propyl-2"methylindol-3"-yl)phthalide A mixture of 8.5 g 2'-carboxy-4-diethylamino-2-ethoxybenzophenone, 4.3 g 1-n-propyl-2-methylindole, and 12 ml of acetic anhydride is stirred at 100° C for 3 hours. After the addition of 1.7 ml of water the mixture is cooled to 20° C and diluted with 35 ml of methanol. The precipitated solid is filtered off, washed with methanol, and dried, yielding 9.3 g (75% of the theory) of the phthalide as a white solid, m.p. 138°–9° C; λ max in 95% acetic acid = 576 nm and 385 nm. Solutions of the compound in hydrocarbon organic solvents are colorless and when contacted with attapulgite, silica or silton clay develop a powerful violet-blue color and with a phenolic resin a deep blue color is obtained. Reflectance curves of the image on silton clay paper showed absorption maxima at λ 582 and 398 nm and on phenolic resin paper at λ 585 nm.

EXAMPLE 2

3-(4'-Diethylamino-2'-ethoxyphenyl)-3-(1"-n-octyl-2"-methylindol-3"-yl)phthalide A mixture of 16.0 g 3-(2'-carboxybenzoyl)-1-n-octyl-2-methylindole, 7.8 g 3-(N,N-diethylamino)phenetole, and 19 ml of acetic anhydride is stirred at 100° C for 3 hours, then cooled to 25° C. After the addition of water and methanol an oily mass is obtained from which the aqueous liquors are then decanted. The oil is taken up in hot petroleum ether and the solution is then dried with $Na_2SO_4$, filtered, and left to cool, whereupon a crystalline product is obtained. This is filtered off, washed with methanol and dried to yield 11.0 g (48% of theory) of the phthalide as a white solid, m.p. 93°–7° C, λ max in 95% acetic acid = 579 and 385 nm. Solutions in hydrocarbon solvents are colorless and give violet-blue colors when contacted with attapulgite, silica or silton clay; and deep blue on phenolic resin. Reflectance curves on clay paper show absorption maxima at λ 582 and 398 nm and on phenolic resin paper at λ 602 nm.

EXAMPLE 3

3(4'-Diethylamino-2'-acetoxyphenyl)-3-(1"-ethyl-2"-methylindolyl-3")-phthalide A mixture of 31.3 g 2'-carboxy-4-diethylamino-2-hydroxybenzophenone, 16.1 g 1-ethyl-2-methylindole and 47 ml of acetic anhydride is stirred at 100° for 4.5 hours then cooled to 50° C. 5.4 ml of water are added and the mixture is cooled to 25° C over 1.5 hours. After the addition of 38 ml of methanol and 25 ml of water followed by further stirring, a precipitate is filtered off, washed with methanol, and dried to yield 35.8 g (72% of the theory) of color former. M.p. 163°–165° C. Reflectance curves on clay paper give absorption maxima at λ 598 and 410 nm and on phenolic resin at λ 610 nm.

The phthalide compounds of the formula

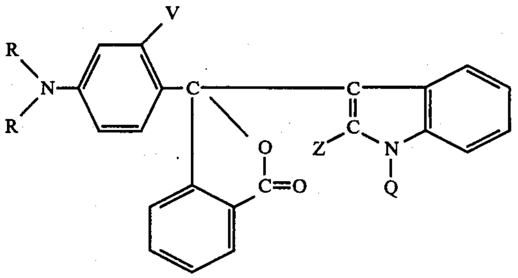

(12)

listed in the table below can be manufactured similarly.

Table I

| Ex. | R | V | Z | Q | m.p.° C | λ max (nm) acetic acid | Silton | phenolic resin |
|---|---|---|---|---|---|---|---|---|
| 4 | $C_2H_5$ | $CH_3$ | $CH_3$ | n-$C_5H_{11}$ | 140–141 | 600 | 602 | 609 |
| 5 | $C_2H_5$ | $CH_3$ | $CH_3$ | n-$C_6H_{13}$ | 149–150 | 600 | 605 | 612 |
| 6 | $C_2H_5$ | $CH_3$ | $CH_3$ | n-$C_7H_{15}$ | 121–122 | 600 | 600 | 608 |
| 7 | $C_2H_5$ | $CH_3$ | $CH_3$ | n-$C_8H_{17}$ | 107–108 | 598 | 600 | 609 |
| 8 | $C_2H_5$ | $CH_3$ | $CH_3$ | n-$C_3H_7$ | 142–144 | 598 | 600 | 609 |
| 9 | $C_2H_5$ | $CH_3$ | $CH_3$ | n-$C_4H_9$ | 114–115 | 600 | 601 | 609 |
| 10 | $C_2H_5$ | $CH_3$ | 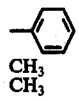 | n-$C_3H_7$ | 175–176 | 612 | 617 | 616 |
| 11 | $C_2H_5$ | $OCH_3$ | $CH_3$ | n-$C_3H_7$ | 133–134 | 580 | 585 | 595 |
| 12 | $C_2H_5$ | $OCH_3$ | $CH_3$ | n-$C_4H_9$ | 73–75 | 578 | 585 | 595 |
| 13 | $C_2H_5$ | $OCH_3$ | 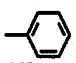 | n-$C_3H_7$ | 65–66 | 580 | 600 | 598 |
| 14 | $C_2H_5$ | $OC_2H_5$ | $CH_3$ | n-$C_4H_9$ | 151–152 | 578 | 580 | 591 |
| 15 | $C_2H_5$ | $OC_2H_5$ | $CH_3$ | n-$C_5H_{11}$ | 111–112 | 578 | 582 | 590 |
| 16 | $C_2H_5$ | $OC_2H_5$ | $CH_3$ | n-$C_6H_{13}$ | 121–122 | 578 | 582 | 592 |
| 17 | $C_2H_5$ | $OC_2H_5$ | $CH_3$ | n-$C_7H_{15}$ | 114–115 | 578 | 582 | 592 |
| 18 | $C_2H_5$ | $OC_2H_5$ | $CH_3$ | 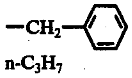 | 156–157 | 572 | 580 | |
| 19 | $C_2H_5$ | $OC_2H_5$ | 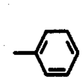 | n-$C_3H_7$ | 151–152 | 585 | 586 | 594 |
| 20 | $C_2H_5$ | $OC_2H_5$ | 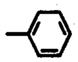 | n-$C_4H_9$ | 78 | 685 | 588 | 594 |
| 21 | $C_2H_5$ | $OC_2H_5$ | 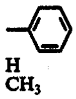 | n-$C_5H_{11}$ | 118–120 | 584 | 589 | 594 |
| 22 | $C_2H_5$ | $OC_2H_5$ | H | n-$C_6H_{13}$ | 120–121 | 584 | 589 | 594 |
| 23 | 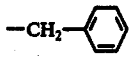 | $OCH_3$ | $CH_3$ | $C_2H_5$ | 93 | 579 | 581 | 586 |
| 24 | 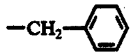 | $OCH_3$ | $CH_3$ | n-$C_3H_7$ | 88–91 | 580 | 581 | 586 |

APPLICATION EXAMPLE 1

Preparation of pressure-sensitive copying paper

A solution of 3 g of 3-(4'-diethylamino-2'-ethoxyphenyl)-3-(1"-n-propyl-2"-methylindol-3"-yl)phthalide in 97 g of hydrogenated terphenyl is emulsified in a solution of 12 g of pigskin gelatine in 88 g of water at 50° C then a solution of 12 g gum arabic in 88 g of water at 50° C is added. The emulsion is diluted by adding 200 ml of water at 50° C and coacervation is brought about by pouring into 600 g of ice-water and stirring for 3 hours. The resulting suspension is coated on paper and dried. When this paper is placed with its coated side adjacent to a sheet of paper coated either with attapulgus clay, silton clay, silica, or phenolic resin and writing or typing is made upon the top sheet a strong blue copy is made upon the co-reactive sheet.

APPLICATION EXAMPLE 2

Preparation of pressure-sensitive copying paper

A solution of 1.8 g of 3-(4'-diethylamino-2'-ethoxyphenyl)-3-(1"-n-butyl-2"-methylindol-3"-yl)phthalide and 1.5 g benzoyl leuco methylene blue in 97 g of hydrogenated terphenyl is emulsified in a solution of 12 g of pigskin gelatine in 88 g of water at 50° C then a solution of 12 g gum arabic in 88 g of water at 50° C is added. The emulsion is diluted by adding 200 ml of water at 50° C and coacervation is brought about by pouring into 600 g of ice-water and stirring for 3 hours. The resulting suspension is coated on paper and dried. When this paper is placed with its coated side adjacent to a sheet of paper coated either with attapulgus clay, silton clay, or silica, and writing or typing is made upon the top sheet a strong blue copy is made upon the co-reactive sheet. The developed image is dark blue with good contrast and has excellent stability to light and water.

APPLICATION EXAMPLE 3

Preparation of pressure-sensitive copying paper

A solution of 3 g of 3-(4'-diethylamino-2'-ethoxyphenyl)-3-(1"-n-octyl-2"-methylindol-3"-yl)phthalide in 97 g of hydrogenated terphenyl is emulsified in a solution of 12 g of pigskin gelatine in 88 g of water at 50° C then a solution of 12 g gum arabic in 88 g of water at 50° C is added. The emulsion is diluted by adding 200 ml of water at 50° C and coacervation is brought about by pouring into 600 g of ice-water and stirring for 3 hours. The resulting suspension is coated on paper and dried. When this paper is placed with its coated side adjacent to a sheet of paper coated either with attapulgus clay, silton clay, silica, or phenolic resin and writing or typing is made upon the top sheet a strong blue copy is made upon the co-reactive sheet.

APPLICATION EXAMPLE 4

Preparation of pressure-sensitive copying paper

A solution of 2.1 g of 3-(4'-diethylamino-2'-ethoxyphenyl)-3-(1"-n-octyl-2"-methylindol-3"-yl)phthalide and 1.5 g benzoyl leuco methylene blue in 97 g of hydrogenated terphenyl is emulsified in a solution of 12 g of pigskin gelatine in 88 g of water at 50° C then a solution of 12 g gum arabic in 88 g of water at 50° C is added. The emulsion is diluted by adding 200 ml of water at 50° C and coacervation is brought about by pouring into 600 g of ice-water and stirring for 3 hours. The resulting suspension is coated on paper and dried.

When this paper is placed with its coated side adjacent to a sheet of paper coated either with attapulgus clay, silton clay, or silica, and writing or typing is made upon the top sheet a strong blue copy is made upon the co-reactive sheet. The developed image is dark blue with good contrast and has excellent stability to light and water.

Similar effects are obtained by using any phthalide compound listed in Table I.

We claim:

1. A phthalide compound of the formula

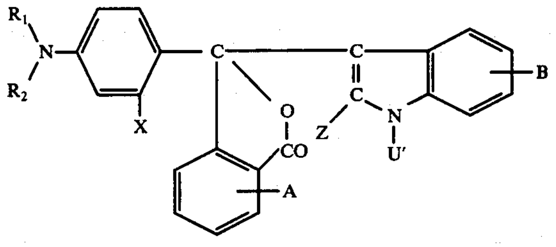

wherein $R_1$ and $R_2$, independently of the other, represent hydrogen, alkyl with 1 to 12 carbon atoms, alkoxyalkyl with 2 to 8 carbon atoms, cycloalkyl with 5 or 6 carbon atoms, benzyl or phenyl, X represents alkyl with 1 to 12 carbon atoms, alkoxy with 1 to 12 carbon atoms or alkanoyloxy with 2 to 4 carbon atoms, Z represents hydrogen, alkyl having 1 to 12 carbon atoms or phenyl, U' represents alkyl having 7 to 12 carbon atoms, benzyl or β-cyanoethyl, and A and B represent hydrogen, dimethylamino, diethylamino or n-hexylamino and B also represents nitro or halogen.

2. A phthalide compound according to claim 1, wherein U' represents alkyl having 7 to 12 carbon atoms.

3. A phthalide compound according to claim 1, of the formula

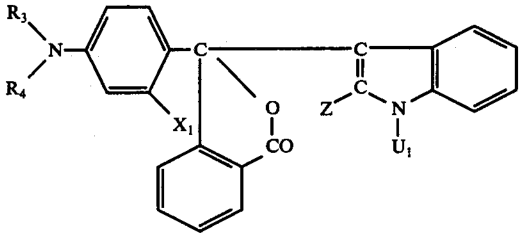

wherein $R_3$ and $R_4$ independently of the other represent hydrogen, alkyl with 1 to 4 carbon atoms, cyclohexyl, benzyl or phenyl, $X_1$ represents methyl, alkoxy with 1 to 12 carbon atoms, or alkanoyloxy with 2 to 4 carbon atoms, $Z_1$ represents hydrogen, alkyl having 1 to 4 carbon atoms or phenyl, $U_1$ represents alkyl having 7 to 8 carbon atoms or benzyl.

4. A phthalide compound according to claim 3, of the formula

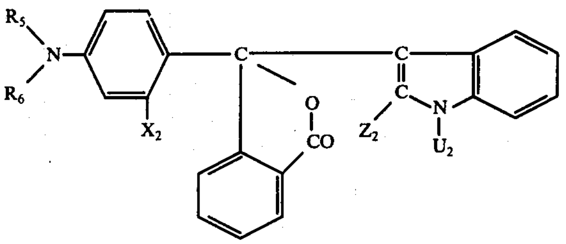

wherein $R_5$ and $R_6$ independently of the other represent alkyl with 1 to 4 carbon atoms or benzyl, $X_2$ represents methyl, alkoxy with 1 to 4 carbon atoms or alkanoyloxy with 2 to 4 carbon atoms, $Z_2$ represents methyl or phenyl and $U_2$ represents alkyl having 7 or 8 carbon atoms.

5. A phthalide according to claim 4, of the formula

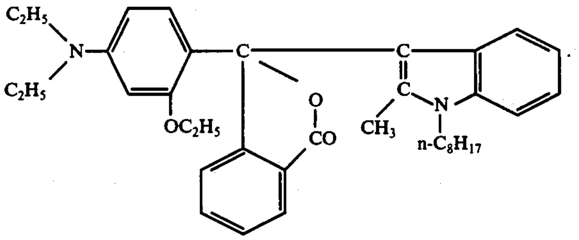

6. A phthalide compound of formula

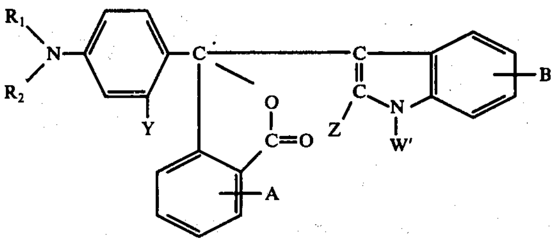

wherein $R_1$ and $R_2$, independently of the other, represent hydrogen, alkyl with 1 to 12 carbon atoms, alkoxyalkyl with 2 to 8 carbon atoms, cycloalkyl with 5 to 6 carbon atoms, benzyl or phenyl, Y represents alkyl having 2 to 12 carbon atoms, alkoxy having 3 to 12 carbon atoms, or alkanoyloxy with 2 to 4 carbon atoms, W' represents alkyl having 7 to 12 carbon atoms and A and B represent hydrogen, dimethylamino, diethylamino or n-hexylamino and B also represents nitro or halogen.

7. A phthalide compound according to claim 6, of the formula

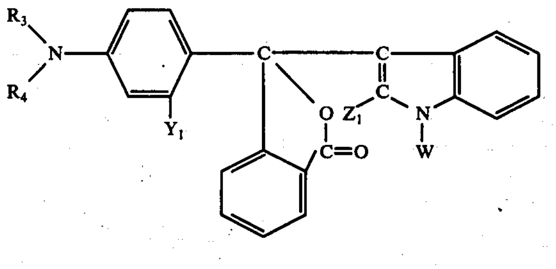

wherein $R_3$ and $R_4$ independently of the other represent hydrogen, alkyl with 1 to 4 carbon atoms, cyclohexyl, benzyl or phenyl, $Z_1$ represents hydrogen, alkyl having 1 to 4 carbon atoms or phenyl, W represents alkyl having 7 to 8 carbon atoms and $Y_1$ represents alkoxy with 3 to 12 carbon atoms or alkanoyloxy with 2 to 4 carbon atoms.

8. A phthalide compound according to claim 7, of the formula

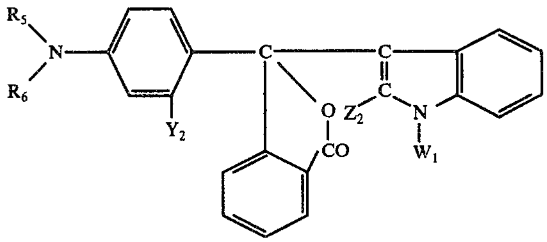

wherein $R_5$ and $R_6$ independently of the other represent alkyl with 1 to 4 carbon atoms or benzyl, $Z_2$ represents methyl or phenyl, $Y_2$ represents alkanoyloxy with 2 to 4 carbon atoms and $W_1$ represents alkyl having 7 or 8 carbon atoms.

* * * * *